United States Patent [19]
Lauttamus

[11] Patent Number: 5,274,847
[45] Date of Patent: Jan. 4, 1994

[54] NOSE PROTECTOR

[76] Inventor: Richard A. Lauttamus, 281 Kerrybrook Drive, Richmond Hill, Ontario, Canada, L4C 3R2

[21] Appl. No.: 858,217

[22] Filed: Mar. 26, 1992

[51] Int. Cl.⁵ .............................................. A41D 13/00
[52] U.S. Cl. ...................................................... 2/9; 2/206
[58] Field of Search ................... 2/9, 12, 13, 206, 15, 2/2; 602/74; 351/132, 138

[56] References Cited

U.S. PATENT DOCUMENTS

| | | | |
|---|---|---|---|
| D. 139,947 | 1/1945 | Saponoff | D2/627 |
| 505,653 | 9/1893 | Gumeson | 2/206 |
| 1,048,191 | 12/1912 | Maurice . | |
| 1,436,313 | 11/1922 | Hafer | 2/206 |
| 1,761,664 | 6/1930 | Harris | 2/206 |
| 1,810,027 | 6/1931 | Moran et al. | D2/627 X |
| 1,962,818 | 6/1934 | Hoffman | 2/12 |
| 2,037,772 | 4/1936 | Everett et al. | 2/206 |
| 2,197,973 | 4/1940 | Everett et al. | 2/12 |
| 2,233,698 | 3/1941 | Girouard | 2/206 |
| 2,364,354 | 12/1944 | Felch | 2/206 |
| 2,519,561 | 8/1950 | Gillman et al. | 2/206 |
| 2,758,506 | 8/1956 | McNeil | 2/13 |
| 3,266,056 | 8/1966 | De Villers et al. | 2/12 |
| 3,271,778 | 9/1966 | Ferguson | 2/12 |
| 3,346,875 | 10/1967 | Weisberger | 2/9 |
| 3,594,813 | 7/1971 | Sanderson | 2/2 |
| 4,387,471 | 6/1983 | Hsu et al. | 2/10 |
| 4,674,133 | 6/1987 | Oschner | 2/206 |
| 4,786,159 | 11/1988 | Piazza | 351/132 |
| 4,912,779 | 4/1990 | Laird | 2/12 |
| 4,976,532 | 12/1990 | Nyman | 2/13 |

FOREIGN PATENT DOCUMENTS

| | | | |
|---|---|---|---|
| 875038 | 9/1941 | France | 2/206 |
| 2577419 | 8/1986 | France | 2/12 |

OTHER PUBLICATIONS

"Sun Guard" nose protector No. 122 sold in packages bearing Canadian and U.S. addresses. The applicant is only aware of sales in Canada in 1990.

Primary Examiner—Clifford D. Crowder
Assistant Examiner—Amy B. Vanatta
Attorney, Agent, or Firm—Brian W. Gray

[57] ABSTRACT

A device to protect the wearer's nose from sunlight, to be attached to glasses or goggles. The device is constructed from a single piece of flexible, creasable sheet material, and has a nose shield and a strap extending from the top of the nose shield. The strap is looped over the bridge of the eyewear and threaded through an aperture at the top of the nose shield. There are locking projections along the edges of the strap that help to secure the strap in the aperture.

24 Claims, 7 Drawing Sheets

NOSE PROTECTOR

FIELD OF THE INVENTION

This invention relates to nose protectors for shielding the nose from such elements as sunlight.

BACKGROUND OF THE INVENTION

A variety of nose protectors are known.

U.S. Pat. Nos. 3,594,813 and 4,674,133 describe nose protectors that can be used without attachment to eyewear such as sunglasses, prescription eyeglasses, etc. Both devices require an adhesive on the underside that attaches directly to the nose skin. Although U.S. Pat. No. 3,594,813 specifies ventilation by through-pores and U.S. Pat. No. 4,674,133 specifies a breathable material, each of these devices would trap heat and be uncomfortable. Sweat and skin oils would decrease the ability of the adhesive to stick to the skin. Facial movements such as wrinkling the nose while squinting might cause the device to detach. The adhesive and, in addition, the sunblocker of U.S. Pat. No. 4,674,133 could cause irritation, mottling, allergic rash, pimples or other complexion problems.

U.S. Pat. No. 3,346,875 describes a nose and lip protecting apparatus to be suspended from eyeglasses. The nose and lip shields are connected by a hinge assembly and the lip shield may be detached. The device may be uncomfortable because the lip shield protrudes into the mouth, and may as well be cumbersome or unattractive. The device does not attach firmly to the glasses and may be dislodged by an active wearer.

U.S. Pat. No. 1,048,191 describes a sun shield for the nose that is secured by a pair of inwardly extending tongues of springy material that clasp the bridge of the nose. As recited earlier, such direct contact with the wearer's face may irritate the skin at the attachment points, may cause discomfort and sweating, and may be easily dislodged, even by facial movements.

U.S. Pat. Nos. 2,519,561 and 4,786,159 describe nose protectors that require attachment to particular types of eyeglasses. The glasses and nose protector described in U.S. Pat. No. 2,519,561 have complementary lug-like projections and apertures at the bridge that snap together to secure the device. Standard glasses or goggles lacking projections or apertures are generally not suitable for use with this nose protector. U.S. Pat. No. 4,786,159 describes a pair of eyeglasses with two positions at which the nose protector can be attached, preferably by a snap fastener. In one position the nose protector covers the wearer's nose, and in the other it is stowed beneath the glasses at the bridge.

U.S. Pat. No. 1,962,818 describes a nose protector that suspends from the bridge of glasses by spring hook-like members. It is relatively complicated in that it cannot be manufactured in one piece, but requires the separate construction of the shield and the hooks, followed by their attachment.

The nose protectors described in U.S. Pat. Nos. 2,197,973 and 2,233,698 can be constructed in a single piece. However, they require curving hooks or flanges for attachment to glasses and therefore cannot be constructed from flat material. In addition, their methods of attachment allow for easy dislodgement of the device by an active wearer.

U.S. Pat. No. 2,364,354 describes a nose protector that can be formed from a single piece of flat material. However, the device requires an assembly process involving folds, tabs and slots, which produces a cumbersome and unattractive end-product.

SUMMARY OF THE INVENTION

The present invention provides, in one broad aspect, a nose protector for use with eyewear, having a nose shield and a flexible member attached thereto for looping around the eyewear, and having an aperture sufficiently spaced from a free end of the flexible member such that the flexible member may be looped around a portion of the eyewear and passed through the aperture to secure the nose protector to the eyewear. The nose shield and flexible member may be formed from a single piece of flexible, creasable sheet material.

In another broad aspect, the invention provides a nose protector for use with eyewear that is made from a single piece of flexible, creasable sheet material and that has at its lower end a nose shield portion tapering from bottom to top, the nose shield having an aperture near its top, and a strap portion extending from the top of the nose shield portion, the strap being of a width to fit through the aperture in the nose shield and long enough to encompass at least a portion of the bridge of an article of eyewear when looped back on itself and inserted in the aperture.

In certain other broad aspects, the invention provides a nose protector for use with eyewear that has at its lower end a nose shield portion tapering from bottom to top, a strap portion extending from the top of the nose shield portion, the strap being of a length sufficient to encompass at least a portion of the bridge of an article of eyewear when looped back on itself, and pressure-sensitive adhesive means, such that the means may be pressed to another portion of the nose protector to secure the nose protector to the eyewear when the strap is looped around the portion of the eyewear and back on itself.

The invention may further provide that the flexible member or strap has a plurality of projections, such that the projections are retained against a portion of the nose protector to fasten the nose protector to the eyewear when the strap is passed through the aperture. The aperture may be a slit. The aperture may be at or near the junction of the nose shield and the flexible member, or in the nose shield.

The width of the projections may be of the same size or slightly larger than the aperture, such that when pulled through the aperture the projections prevent disengagement of the strap from the aperture. The projections may be angled downwardly on either side of the strap so as to pass into the slit in one direction and to abut the ends of the slit in the other direction, thus preventing disengagement of the strap. The projections may lie at an approximately 45° angle to the longitudinal axis of the strap, and the outside edge of each projection may be rounded. The strap may be tearable at a projection that has passed through the slit.

A small circle may be cut out at each end of the slit aperture. The small circles may be die- or punch-cut.

In certain embodiments, the nose protector may have a tag at an end opposite to the nose shield. The tag may be tearable, and removing the tag may release a free end of the flexible member or strap, which can be threaded through the aperture. The tag may contain means to hang the nose protector for storage or display purposes. The tag may have an opening in it, and a cut may extend from the opening to the perimeter of the tag.

The nose shield of the nose protector may be creased or creasable along its center line to create an indentation along that line for receiving the bridge of a nose when the nose protector is installed on eyewear. The nose shield may be lightly scored along its center line to facilitate its creasing. The nose shield may be shovel- or bell-shaped.

The flexible, creasable sheet material of the nose protector may have a grain or flow parallel to the longitudinal axis of the nose protector. The material may be polypropylene. Alternatively, it may be TESLIN®.

BRIEF DESCRIPTION OF THE DRAWINGS

Certain embodiments of the invention are described, reference being made to the accompanying drawings wherein.

DETAILED DESCRIPTION OF A PREFERRED EMBODIMENT

The disclosed device is for use to protect an individual's nose from exposure to such elements as sunlight. This nose protector can be mounted on eyewear such as prescription eyeglasses, sunglasses, safety glasses, goggles and masks. The device may be decorated for purposes of identification, ornamentation or advertising.

Figure 1:
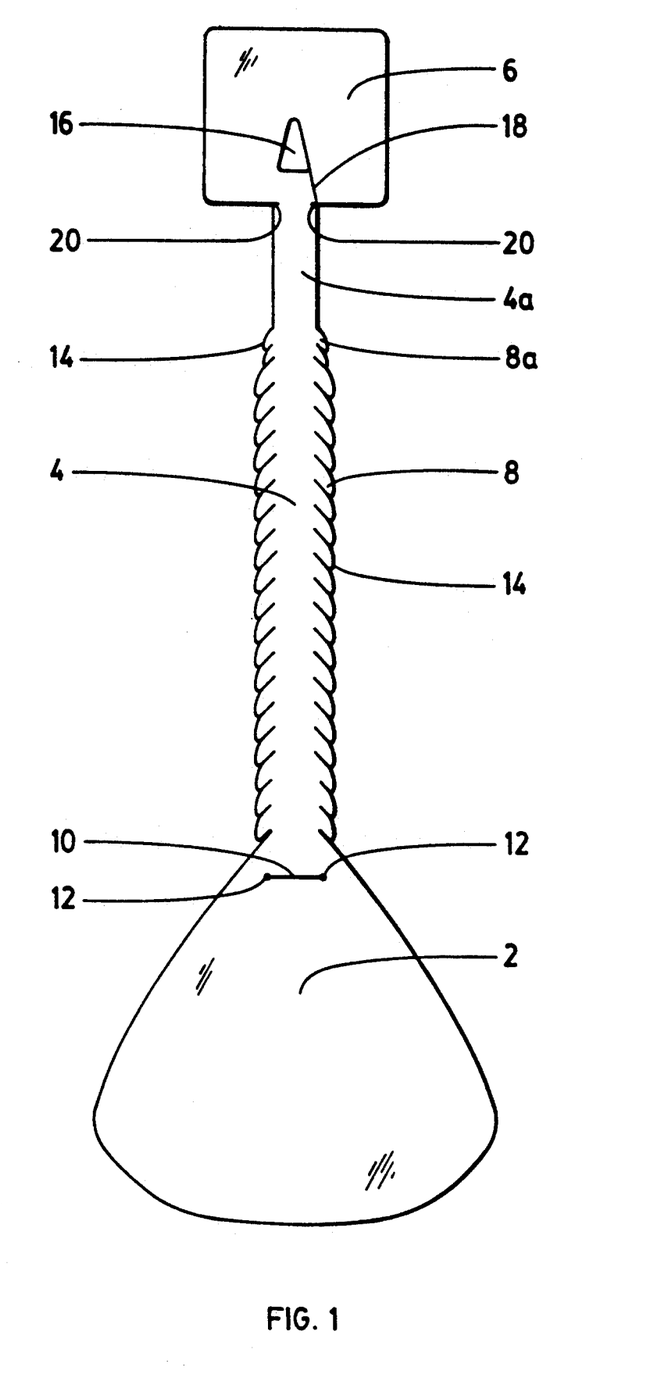
FIG. 1 is a front plan view of a preferred embodiment of the invention prior to mounting on eyewear.

FIG. 1 illustrates a preferred embodiment of the nose protector prior to mounting on eyewear 30. Nose shield 2, locking strap 4 and tag 6 are contiguous, being die-cut as a single unit from the same piece of thin, flexible, creasable, tearable sheet material. Nose shield 2 is shovel- or bell-shaped and can be manufactured in a size and shape suitable for the majority of people. However, it can be easily altered or customized using scissors or a razor knife. Locking wings 8 protrude from the edges of locking strap 4 at an approximately 45° angle, along a major part of the strap's length beginning at nose shield 2. Slit aperture 10 exists in nose shield 2 near the junction of nose shield 2 and locking strap 4, and is oriented perpendicular to locking strap 4. In this embodiment, slit aperture 10 is shorter than the width of locking wings 8 at their tips, but longer than the width at their base. At each end of slit aperture 10 is die- or punch-cut circle 12 to ease expansion of slit aperture 10 and minimize tearing when locking strap 4 is pulled through slit aperture 10 during mounting of the device on eyewear 30.

In this embodiment, slit aperture 10 is a razor edge knife cut to produce an extremely narrow opening for locking strap 4. A larger opening such as a round hole would not be preferred for at least five reasons: i) It would let sunlight in, producing a "hot spot" on the wearer's nose. ii). It would reduce the strength and amount of material at a critical position. iii) It would not allow effective working of locking wings 8, producing a sloppy final fit. iv) It would interfere with any ornamentation or message printed on nose shield 2. v) It would be more obvious than a slit and thus unattractive. For similar reasons, die- or punch-cut holes 12 are extremely small.

In a preferred embodiment, the invention is made with the grain or flow of the sheet material parallel to the longitudinal axis of the nose protector. Cutting or tearing across the grain or flow of a given material is more difficult than tearing along the grain. Thus, in this preferred embodiment slit aperture 10 is perpendicular to the grain of the material, and is less likely to tear, even during several rounds of mounting on eyewear 30, removal and remounting.

Locking strap 4 may be of variable length to accommodate different kinds and sizes of eyewear 30. Preferably, it should be in the range of 2 to 12 inches, with a minimum length of approximately one/half inch. Referring again to FIG. 1, which is drawn to scale, initial short length 4a of locking strap 4 adjacent to tag 6 lacks locking wings 8. Initial group 8a of locking wings 8 after initial short length 4a has short locking wings 8a. All locking wings 8, 8a have rounded outside leading edges 14 to help ease each locking wing through slit aperture 10.

Tag 6 is characterized by opening 16, here shown as a triangular shape, which is located at or near the center of tag 6. Opening 16 allows the nose protector to be hung from a rod or hook, for example in a sales display. Cut 18 extends from opening 16 to the perimeter of tag 6. This allows a nose protector at the back of a rod to be removed without removing any other nose protectors that precede it on the rod. Tag 6 may have a price, product name, assembly instructions, etc. printed on it.

At the base of tag 6 are two other cuts 20 which continue the line of the tag perimeter a short way into the material at the top of looking strap 4. These cuts 20 ease removal of tag 6 from the device and also provide a clean edge and taper on locking strap 4 to ease insertion of locking strap 4 into slit aperture 10.

Figure 2:
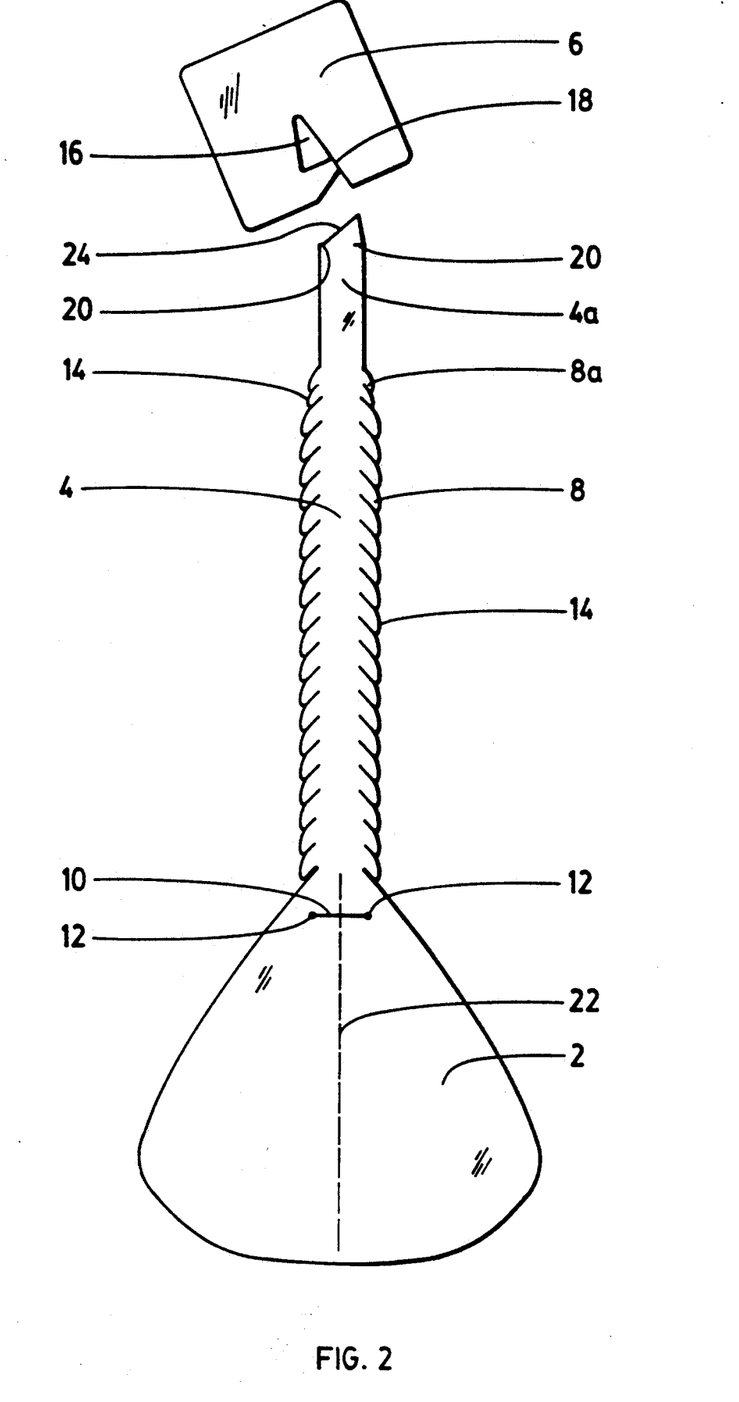
FIGS. 2 to 5 show sequentially stages of mounting of the Preferred embodiment on eyewear.

FIG. 2 illustrates initial assembly steps of the nose protector. Tag 6 is removed from locking strap 4 by cutting with scissors or knife or tearing gently with fingers horizontally between two cuts 20. Before or after tag removal, nose shield 2 is folded or creased longitudinally at center line 22. Preferably, nose shield 2 is lightly scored along center line 22, for instance by a die strike, to facilitate correct folding, and the scoring extends above slit aperture 10.

Figure 3:
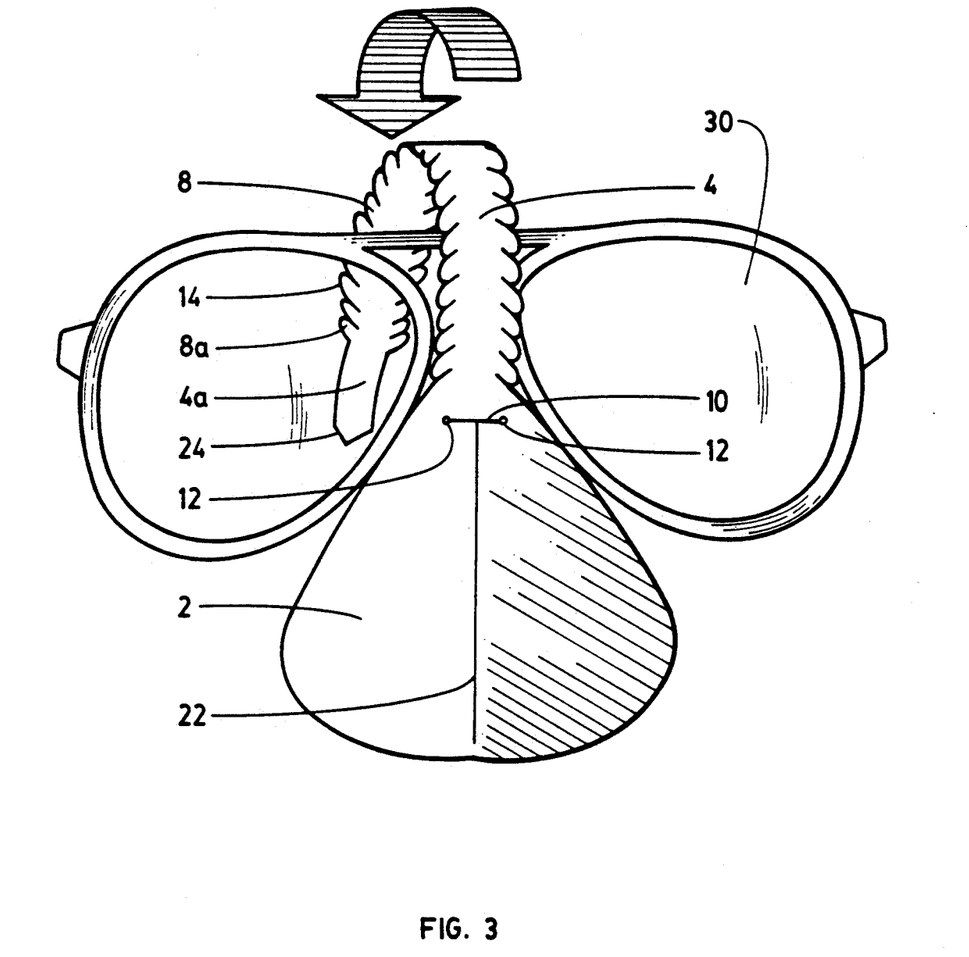

As shown in FIG. 3, end 24 of locking strap 4 that was freed by tag 6 removal is looped over eyewear 30. End 24 is then inserted into slit aperture 10 and locking strap 4 is gently pulled through slit aperture 10. The beginning of this step is facilitated by the lack of locking wings 8 on initial short length 4a of locking strap 4 and by initial group of small locking wings 8a. Locking wings 8 that are not part of initial group 8a are a little larger than slit aperture 10, to provide mechanical interference that ensures a snug fit. Given the relative size of locking wings 8, a slight rocking motion from side to side during pulling of locking strap 4 helps locking wings 8 to move easily through slit aperture 10 with minimum tearing.

Nose shield 2 and/or eyewear 30 should preferably be held firmly at the completion of the pulling step to ensure a snug and secure fit of the nose Protector on eyewear 30. At this juncture locking wings 8 have three types of retaining functions: i) They prevent disengagement of locking strap 4 from slit aperture 10. ii) They help to prevent movement of the nose protector on eyewear 30 and the wearer's face. iii) They maintain the folded shape of nose shield 2 that was produced by creasing along center line 22 by holding creased nose shield 2 within the approximately 90° angle created by the two approximately 45° angles of a locking wing 8 pair.

Figure 5:
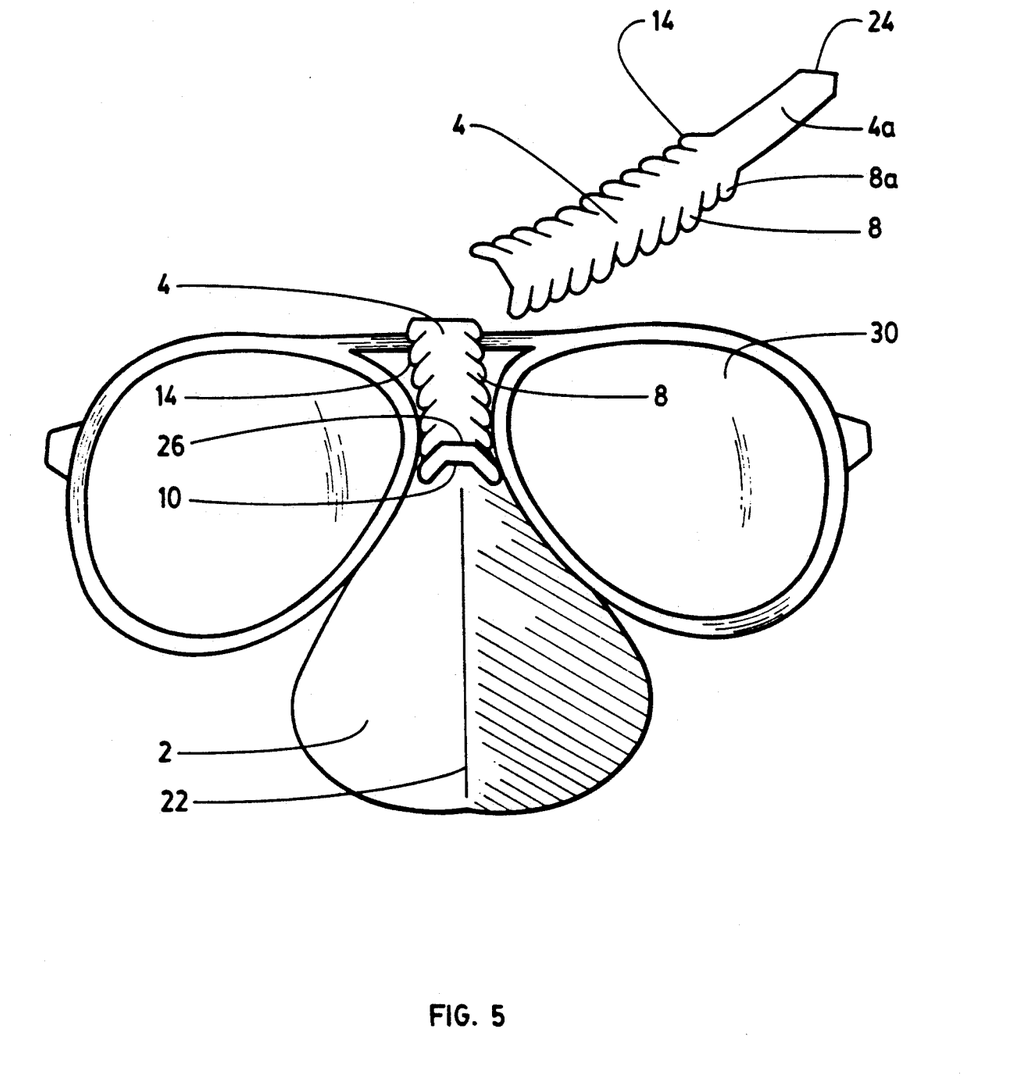

After the desired fit of nose protector on eyewear 30 is achieved, excess locking strap can be trimmed off by cutting or tearing horizontally as shown as FIG. 5, to remove any obstruction of vision and to create a more pleasing appearance. Trimmed end 26 of locking strap 4 remains on the exterior face of nose shield 2.

Figure 4:
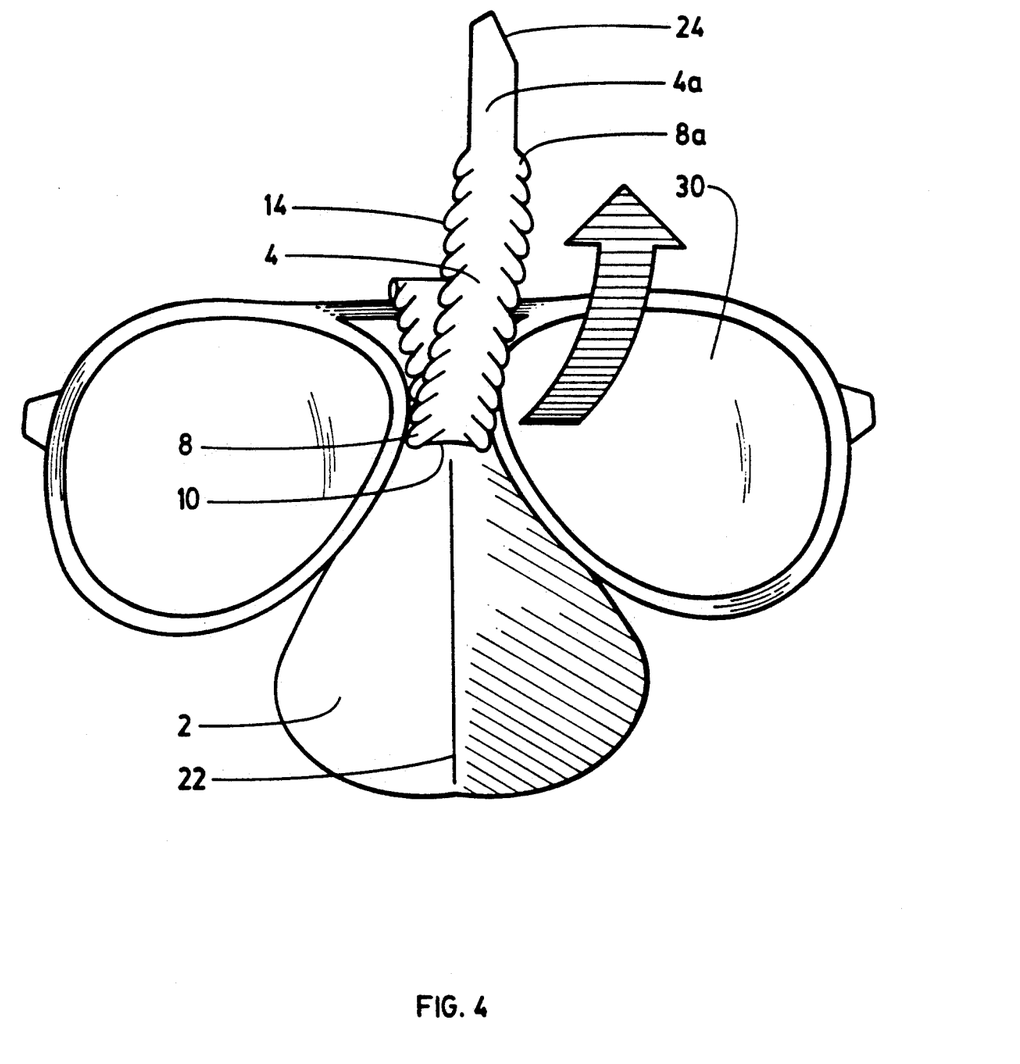
Figure 6:
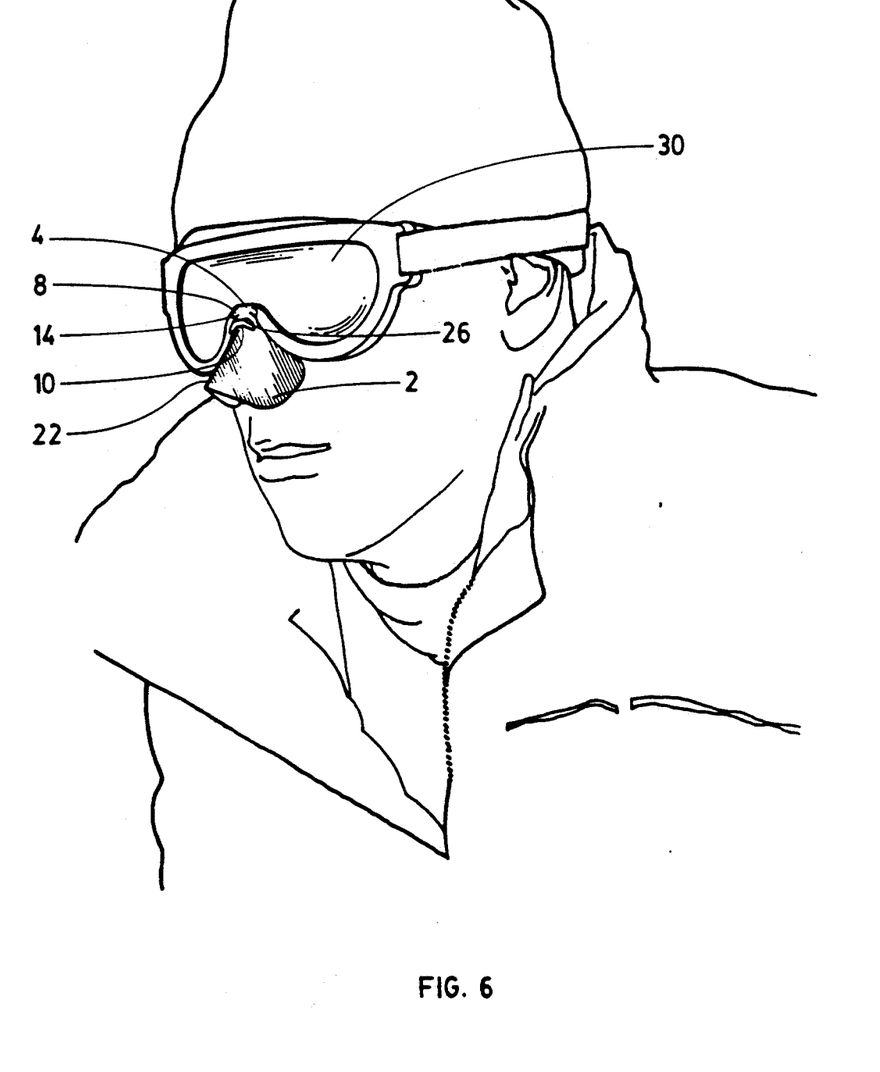
FIG. 6 is a perspective view from the front and side of the preferred embodiment mounted on eyewear.

In FIG. 6, the nose protector is shown in use, looped over and mounted on eyewear 30 worn by a person. Eyewear 30 in this figure is of a different type than in FIGS. 3-5, to illustrate an alternative manner of mounting the nose protector on eyewear. In FIGS. 3-5, locking strap 4 is looped around the entire bridge of eyewear 30. In contrast, in FIG. 6 locking strap 4 is looped around only a portion of this area. Specifically, locking strap 4 is inserted through an opening between the rim, which may have foam rubber padding, and the lens area of eyewear (ski goggles) 30.

It should be obvious that locking strap 4 can be looped under eyewear, rather than over it as described above, but this is not preferred. Looping locking strap 4 under eyewear 30 would result in trimmed end 26 of locking strap 4 being in direct and constant contact with the wearer's face, with potential for discomfort and abrasion. Looping locking strap 4 over eyewear 30 results in trimmed end 26 being on the exterior.

In order to remove the nose protector, locking wings 8 can be squeezed or folded with fingertips and locking strap 4 gently drawn back through slit aperture 10. The device can be easily saved and stored without damage for later reuse, in such places as a pocket, wallet or purse, or can be looped around an eyeglass retaining cord.

The nose protector may be constructed from a variety of natural or manmade materials with suitable properties for the activity during which it will be worn. For example, a nose protector of opaque paper would be suitable to block the sun during certain outdoor activities, but would not be suitable during swimming or in rain. In a second example, the nose protector should not become brittle if it is to be used in severe cold. A discussion of important material properties to be considered follows.

The material should be flexible, creasable, lightweight, inexpensive, long-wearing, opaque to ultraviolet radiation, and resistant to damage from folding. It should be easy to cut during manufacture and tag removal, yet not likely to tear during mounting. The material should be thin but sufficiently rigid, and have memory to hold shape after it is bent. It should be hypoallergenic and its texture should not feel unpleasant on the skin. If ornamentation is desired, the material should be suitable for printing or drawing, as well as abrasion-resistant. The material might be suitably coated after ornamentation to protect the ornamentation. The material might be breathable, water-resistant, and/or recyclable. It may have the ability to retain fragrance. In a preferred embodiment of the invention, the underside of the nose protector has a matte finish and the exterior side has a hard or glossy finish.

In a preferred embodiment of the invention, the nose protector is die-cut from an extruded flat sheet of polypropylene. In a second preferred embodiment of the invention, the nose protector is die-cut from TESLIN ®, a synthetic microporous printing sheet manufactured by PPG Industries of Pittsburgh, Pa. The thickness of the material can vary from 0.002 to 0.050 inches gauge or even thicker, but the optimum thickness for a synthetic plastic appears to be from 0.008 inches gauge to 0.018 inches gauge.

Figure 7:
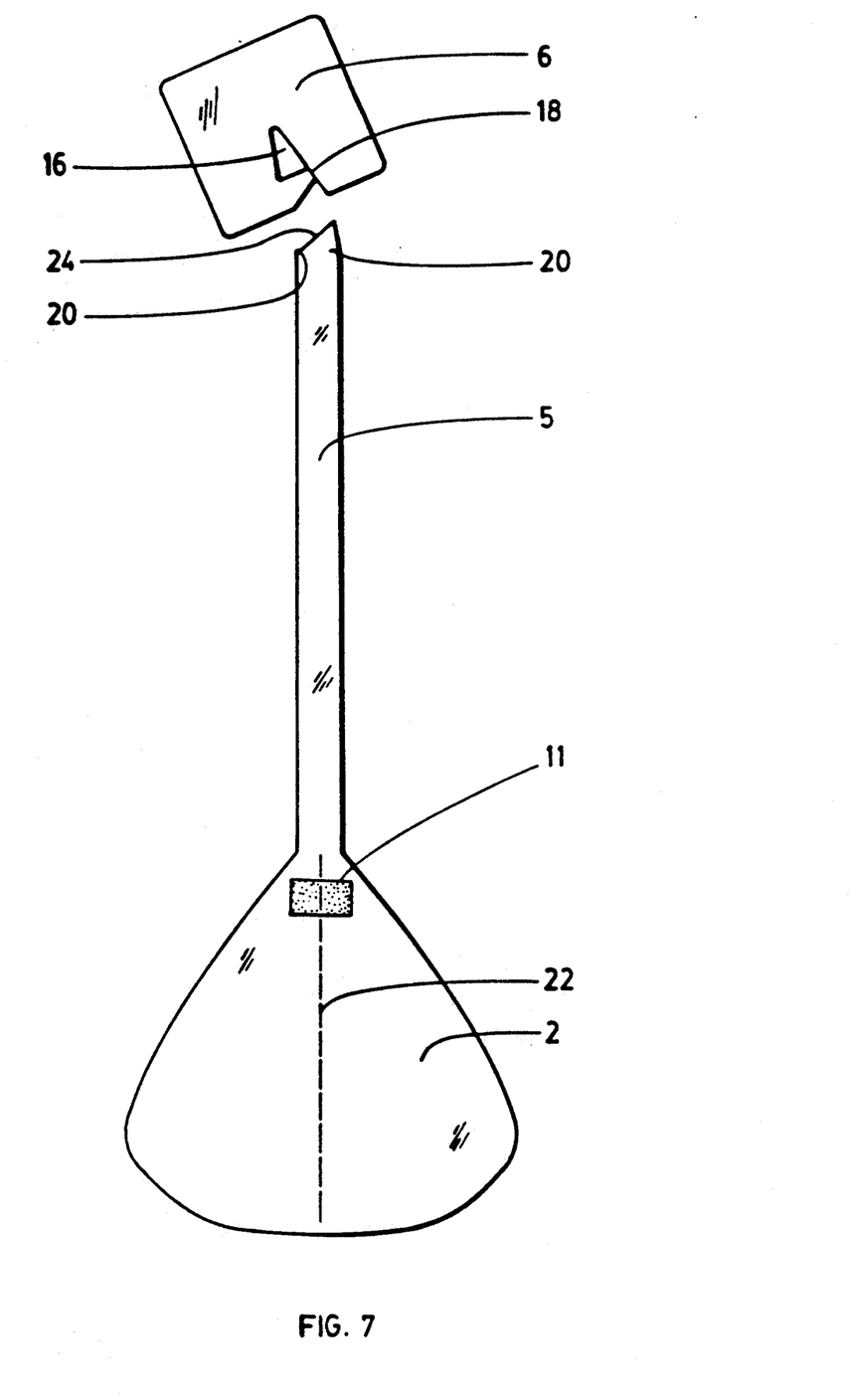
FIG. 7 is a front plan view of a second embodiment of the invention at the same stage of its mounting on eyewear as shown in FIG. 2 for the first embodiment.

In certain embodiments of the invention, the nose protector may be secured to eyewear by any type of pressure-sensitive attachment means, rather than the locking strap-slit aperture means outlined above for the preferred embodiment. Such means may include a pressure-sensitive adhesive, such that after the strap is looped around a portion of the eyewear, two places are pressed together with the fingers to fasten the device. FIG. 7 shows an embodiment of this type, having pressure-sensitive adhesive area 11 that may be secured to strap 5 at any convenient place that provides a snug fit on the eyewear. Pressure-sensitive attachment means may also include VELCRO ® or other hook and loop devices placed on the strap and a matching portion of the nose protector. If the nose protector is creased before the attachment is made, the attachment means may help to hold the nose shield at the desired creased angle, in place of the locking wings.

A design or pattern might be cut out of the nose shield of a nose protector, leading to a suntan or sunburn in this pattern on the wearer's nose.

The nose protector may be lined with, for example, a removable fabric or fur lining.

What is claimed is:

1. A nose protector for use with eyewear, comprising a nose shield and a flexible member attached thereto for looping entirely around the eyewear, and having an aperture sufficiently spaced from a free end of the flexible member such that the flexible member may be looped entirely around a portion of the eyewear and passed through the aperture to secure the nose protector to the eyewear, and wherein the nose shield and flexible member consist of a single piece of flexible, creasable, flat sheet material.

2. The nose protector of claim 1, wherein the flexible member is a strap having a plurality of projections, and wherein the projections are retained against a portion of the nose protector surrounding the aperture to fasten the nose protector to the eyewear when the strap is passed through the aperture.

3. The nose protector of claim 2, wherein the aperture is a slit.

4. The nose protector of claim 3, wherein the aperture is at or near the junction of the nose shield and the flexible member.

5. The nose protector of claim 4, further comprising a tag at an end opposite to the nose shield, the tag for removal prior to securing of the nose protector to eyewear.

6. The nose protector of claim 5, the tag having an opening in it.

7. The nose protector of claim 6, wherein a cut extends from the opening in the tag to the tag perimeter.

8. A nose protector for use with eyewear having a bridge, consisting of a single piece of flexible, creasable, flat sheet material having
   i) at a lower end of the protector, a nose shield portion tapering from bottom to top and having an aperture near the top of such portion; and
   ii) a strap portion extending from the top of the nose shield portion of a width to fit through the aperture in the nose shield and long enough to encompass at least a portion of the bridge when looped back on itself and inserted in such aperture.

9. The nose protector of claim 8, wherein the strap has a plurality of projections whose width is the same size or slightly larger than the aperture, which projections when pulled through the aperture prevent disengagement of the strap from the aperture.

10. The nose protector of claim 9, wherein the aperture is a slit and the projections are angled downwardly towards the lower end of the nose protector and away from the strap on either side of the strap so as to pass into the slit in one direction and to abut the ends of the slit to prevent disengagement of the strap in a second direction.

11. The nose protector of claim 2 or 10, wherein the projections are angled downwardly towards a lower end of the nose protector and away from the strap at an approximately 45° angle to a longitudinal axis of the strap.

12. The nose protector of claim 2 or 10, wherein the projections have outside edges and the outside edge of each projection is rounded.

13. The nose protector of claim 3 or 10, having a small circle cut out at each end of the slit.

14. The nose protector of claim 13, wherein the small circles are die- or punch-cut.

15. The nose protector of claim 8, wherein the strap has a top end and the top end of the strap has tag means formed from the sheet and tearable from the sheet.

16. The nose protector of claim 15, wherein the tag means contains means for hanging the nose protector for storage or display purposes.

17. The nose protector of claim 8, wherein the nose shield is creased or creasable along its center line to create an indentation along that line for receiving the bridge of a nose when the nose protector is installed on eyewear.

18. The nose protector of claim 1 or 17, wherein the nose shield is lightly scored along its center line to facilitate creasing along the center line.

19. The nose protector of claim 3 or 10, wherein the strap is tearable at a projection that has passed through the slit.

20. The nose protector of claim 1 or 8, wherein nose shield is shovel- or bell-shaped.

21. The nose protector of claim 1 or 8, wherein the flexible, creasable sheet material has a grain or flow parallel to a longitudinal axis of the nose protector.

22. The nose protector of 1 or 8, wherein the material is polypropylene.

23. The nose protector of claim 1 or 8, wherein the material is a synthetic microporous sheet material.

24. A nose protector for use with eyewear having a bridge, comprising
  i) at its lower end a nose shield portion tapering from bottom to top;
  ii) a strap portion extending from the top of the nose shield portion, of a length sufficient to encompass at least a portion of the bridge when looped back on itself; and
  iii) pressure-sensitive adhesive means, which means is pressed to another portion of the nose protector to secure the nose protector to the eyewear when the strap is looped around the portion of the bridge and back on itself;
wherein the nose shield and flexible member consist of a single piece of flexible, creasable, flat sheet material.

* * * * *